(12) United States Patent
Seeman et al.

(10) Patent No.: US 7,612,184 B2
(45) Date of Patent: Nov. 3, 2009

(54) POLYNUCLEIC ACID NANOMECHANICAL DEVICE CONTROLLED BY HYBRIDIZATION TOPOLOGY

(75) Inventors: Nadrian Seeman, New York, NY (US); Hao Yan, Durham, NC (US); Xiaoping Zhang, Woodside, NY (US); Zhiyong Shen, Fremont, CA (US)

(73) Assignee: New York University, New York, NY (US)

( * ) Notice: Subject to any disclaimer, the term of this patent is extended or adjusted under 35 U.S.C. 154(b) by 1045 days.

(21) Appl. No.: 10/370,101

(22) Filed: Feb. 21, 2003

(65) Prior Publication Data

US 2003/0219790 A1    Nov. 27, 2003

Related U.S. Application Data

(60) Provisional application No. 60/358,365, filed on Feb. 22, 2002.

(51) Int. Cl.
*C07H 19/00*    (2006.01)
*C12M 1/34*    (2006.01)
*C12M 3/00*    (2006.01)

(52) U.S. Cl. ................. 536/23.1; 435/288.4; 435/288.7

(58) Field of Classification Search ........................ None
See application file for complete search history.

(56) References Cited

OTHER PUBLICATIONS

Yan et al. A robust DNA mechanical device controlled by hybidization topology. Nature, vol. 415, Jan. 3, 2002, pp. 62-65.*
Seeman, DNA nicks and nodes and nanotechnology, *Nano Letters*, 1(1):22-26 (2000).
Mao et al., A nanomechanical device based on the B-Z transition of DNA, *Nature*, 197:144-146 (1999).
Yurke et al., a DNA-fuelled molecular machine made of DNA, *Nature*, 406:605-608 (2000).
Seeman, in the nick of space: Generalized nucleic acid complementarity and DNA nanotechnology, *Synlett*. 11:1536-1548 (2000).

* cited by examiner

*Primary Examiner*—Marjorie Moran
*Assistant Examiner*—Russell S Negin
(74) *Attorney, Agent, or Firm*—Browdy and Neimark, PLLC

(57) ABSTRACT

The present invention is directed to a sequence dependent polynucleotide nanomechanical device based on a nucleic acid paranemic crossover (PX) molecule which is a four-stranded structure related to parallel double crossover molecules, except that every possible crossover takes place. Eliminating two crossovers leads to a topoisomer, termed $JX_2$, in which one pair of ends are switched (rotated 180°) while the other pair of ends remain the same. The device can be cycled between the two states, PX and $JX_2$, by replacing single strands that set the state to be PX or $JX_2$.

15 Claims, 12 Drawing Sheets

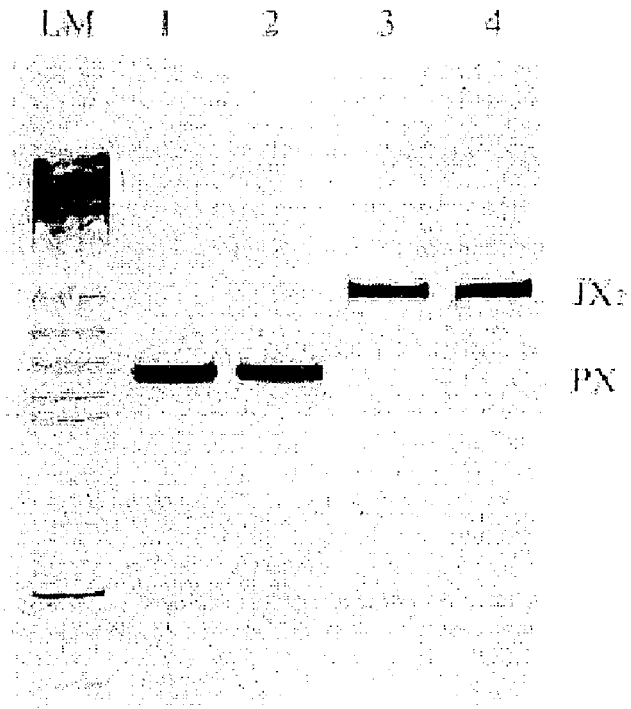
FIG. 8A
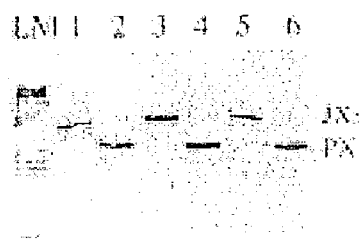
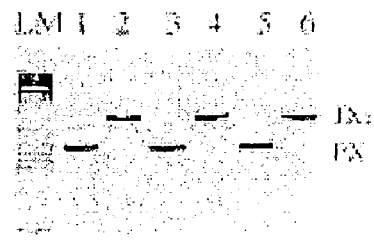
FIG. 8B
FIG. 8C

PX

200x200nm

200x200nm

JX₂

200x200nm

200x200nm

PX  JX₂  PX  JX₂

200x200nm

200x200nm

200x200nm

200x200nm

… (standard patent preamble)

SEQUENCE LISTING

```
<160> NUMBER OF SEQ ID NOS: 15
<210> SEQ ID NO 1
<211> LENGTH: 101
<212> TYPE: DNA
<213> ORGANISM: Artificial Sequence
<220> FEATURE:
<223> OTHER INFORMATION: synthetic
```

```
<400> SEQUENCE: 1
tgccaagcct ccagccacct tttggtggct ggaggaccga tgcggcgcga gtggtaggtg    60
ccgagcacac ctcatgcctt ttggcatgag gtgtatccgc t                       101

<210> SEQ ID NO 2
<211> LENGTH: 101
<212> TYPE: DNA
<213> ORGANISM: Artificial Sequence
<220> FEATURE:
<223> OTHER INFORMATION: synthetic

<400> SEQUENCE: 2
catcggttca ccgcacgtct tttgacgtgc ggtgacttgg caacggttgt gagtacgaca    60
gcggatcgtc cgaatcactt ttgtgattcg gcaggctcgg c                       101

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3
gcaagcagac ctaactcaca cgccg                                         25

<210> SEQ ID NO 4
<211> LENGTH: 25
<212> TYPE: DNA
<213> ORGANISM: Artificial Sequence
<220> FEATURE:
<223> OTHER INFORMATION: synthetic

<400> SEQUENCE: 4
gtcgtccact cgaccgtaga ctagc                                         25

<210> SEQ ID NO 5
<211> LENGTH: 25
<212> TYPE: DNA
<213> ORGANISM: Artificial Sequence
<220> FEATURE:
<223> OTHER INFORMATION: synthetic

<400> SEQUENCE: 5
gtcgtactca caaccgtagt ctaac                                         25

<210> SEQ ID NO 6
<211> LENGTH: 25
<212> TYPE: DNA
<213> ORGANISM: Artificial Sequence
<220> FEATURE:
<223> OTHER INFORMATION: synthetic

<400> SEQUENCE: 6
gcttccagac ctaccactcg cgccg                                         25

<210> SEQ ID NO 7
<211> LENGTH: 25
<212> TYPE: DNA
<213> ORGANISM: Artificial Sequence
<220> FEATURE:
<223> OTHER INFORMATION: synthetic
```

<400> SEQUENCE: 7
cggcgtgtga gttaggtctg cttgc					25

<210> SEQ ID NO 8
<211> LENGTH: 25
<212> TYPE: DNA
<213> ORGANISM: Artificial Sequence
<220> FEATURE:
<223> OTHER INFORMATION: synthetic

<400> SEQUENCE: 8
gctagtctac ggtcgagtgg acgac					25

<210> SEQ ID NO 9
<211> LENGTH: 24
<212> TYPE: DNA
<213> ORGANISM: Artificial Sequence
<220> FEATURE:
<223> OTHER INFORMATION: synthetic

<400> SEQUENCE: 9
gttagactac ggtgtgagta cgac					24

<210> SEQ ID NO 10
<211> LENGTH: 25
<212> TYPE: DNA
<213> ORGANISM: Artificial Sequence
<220> FEATURE:
<223> OTHER INFORMATION: synthetic

<400> SEQUENCE: 10
cggcgcgagt ggtaggtctg gaagc					25

<210> SEQ ID NO 11
<211> LENGTH: 38
<212> TYPE: DNA
<213> ORGANISM: Artificial Sequence
<220> FEATURE:
<223> OTHER INFORMATION: synthetic

<400> SEQUENCE: 11
ctgtggaggt gtcaggcgag accagtggca tctcgtcg					38

<210> SEQ ID NO 12
<211> LENGTH: 38
<212> TYPE: DNA
<213> ORGANISM: Artificial Sequence
<220> FEATURE:
<223> OTHER INFORMATION: synthetic

<400> SEQUENCE: 12
cgacggcacc gcactggtct cggtaccatt atacacag					38

<210> SEQ ID NO 13
<211> LENGTH: 38
<212> TYPE: DNA
<213> ORGANISM: Artificial Sequence
<220> FEATURE:
<223> OTHER INFORMATION: synthetic

<400> SEQUENCE: 13
gcggctataa tggtacgatt gcaggcacgg tgctggcc					38

-continued

```
<210> SEQ ID NO 14
<211> LENGTH: 38
<212> TYPE: DNA
<213> ORGANISM: Artificial Sequence
<220> FEATURE:
<223> OTHER INFORMATION: synthetic

<400> SEQUENCE: 14
ggccaagatg ctgcctgcaa tccctgacac ctcgccgc                              38

<210> SEQ ID NO 15
<211> LENGTH: 40
<212> TYPE: DNA
<213> ORGANISM: Artificial Sequence
<220> FEATURE:
<223> OTHER INFORMATION: synthetic

<400> SEQUENCE: 15
tacgaatcct tcgagcgacg cagccgtgcg aagtagatgc                            40
```

POLYNUCLEIC ACID NANOMECHANICAL DEVICE CONTROLLED BY HYBRIDIZATION TOPOLOGY

CROSS-REFERENCE TO RELATED APPLICATIONS

This application claims the benefit of priority under 35 U.S.C. §119(e) from U.S. provisional application No. 60/358,365, filed Feb. 22, 2002, the entire contents of which are herein incorporated by reference.

GOVERNMENT LICENSE RIGHTS

The experiments performed in this application were supported by the Office of Naval Research, Grant No. N00014-98-1-0093, the National Institute of General Medical Sciences, Grant No. GM-29554, the National Science Foundation/DARPA, Grant No. NSF-CCR-97-25021, the Information Directorate of the Air Force Research Laboratory, Grant No. F30602-98-C-0148, and the National Science Foundation, Grant Nos. CTS-9986512 and EIA-0086015. The U.S. Government has a paid-up license in this invention and the right in limited circumstances to require the patent owner to license others on reasonable terms as provided for by the terms of the above-awarded grants.

BACKGROUND OF THE INVENTION

1. Field of the Invention

The present invention relates to molecular scale mechanical devices.

2. Description of the Related Art

Recent reports of molecular scale devices include systems based on catenanes and rotaxanes (Pease et al., 2001 Jimenez et al., Brouwer et al., 2001), chiroptical molecular switches (Koumera et al., 1999), molecular ratchets (Kelly et al., 1999) and DNA (Mao et al., 1999). These devices are activated by triggers, i.e., redox, small molecule or ionic effectors, light or temperature, that act equally on all devices present.

DNA nanotechnology entails the construction of objects, arrays and devices that utilize unusual motifs. The laboratory of the present inventors reported the first DNA-based nanomechanical device, based on the B-Z (right-hand to left-hand) transition of DNA (Mao et al. 1999). The B to Z transition is activated/deactivated by the presence or absence of high ionic strength or by small molecule effectors, such as $(Co(NH_3)_6)Cl_3$, that facilitate it. This first prototype DNA nanomechanical device consisted of two double crossover molecules of DNA attached to a piece of DNA that could switch from B- to Z-DNA, thereby changing the rotational position of one of the double crossovers by about a half turn, which resulted in atoms moving by 20-60 Angstroms, depending on their distance from the rotation axis. The device was actuated by the addition of a chemical actuator, $Co(NH_3)_6^{+++}$, to the solution, and returned to its original conformation when the $Co(NH_3)_6^{+++}$ was removed.

Assembly of DNA arrays with patterns produced by a variety of components localized according to programmed self-assembly were reported by the laboratory of the present inventors (Winfree et al., 1998; Liu et al., 1999; Mao et al., 1999; LaBean et al., 2000; Sha et al., 2000; Mao et al., 2000). The incorporation of molecular devices into arrays could lead to the complex structural states necessary for nanorobotics, but the activators would need to be localized very tightly to address individual devices. Were N such devices to be incorporated into a 2D or 3D array, there would only be two states, that corresponding to B-DNA and that corresponding to Z-DNA, except perhaps for a small amount of nuance.

It is desirable to be able to produce more structural states within an array, ideally at least $2^N$ states, by, i.e., producing a variety of 2-state devices that can be individually programmed, rather than programmed by the addition of the same chemical. A mechanism to effect this type of control with DNA has been prototyped recently but the system to which it was applied generates by-products and is therefore not robust (Yurke et al., 2000). The Yurke et al. device operates by the addition of a DNA strand of a specific sequence to a partial motif. When doing so, Yurke et al. obtained a population of about 80% monomers of their target complex and 20% dimers. Thus, the products in the Yurke et al. device are only partially stable and partially predictable, i.e., not robust.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a robust nanomechanical device based on a polynucleic acid molecule capable of cycling between two topoisomeric states upon the sequential addition and incubation and incubation of fuel and set strands of nucleic acids. One of the two topoisomeric states is a nucleic acid paranemic crossover (PX) molecule having a coaxial structure of flanking parallel Watson-Crick double helices of nucleic acid strands with two backbones, two pairs of ends, a plurality of major and minor grooves, a central dyad axis, and reciprocal crossovers where two strands of a strand pair from one helix pass over to the other helix and which reciprocal crossovers flank the central dyad axis at every major and minor groove separation where two strands of a strand pair from one helix approach the central dyad axis. Each of the nucleic acid strands is involved in a crossover at the start and the end of a Watson-Crick helical turn.

The $JX_2$ topoisomer differs from the nucleic acid paranemic crossover molecule by having one pair of ends rotated relative to the other pair of ends by 180° and by having two adjacent sites where the two backbones juxtapose without the strands being involved in a crossover.

The nanomechanical device of the present invention is created when a segment of one strand from each strand pair, referred to as a PX set strand, is broken from the rest of the strand in the nucleic acid paranemic crossover (PX) molecule. The nucleic acid paranemic crossover molecule with PX set strands is converted to its $JX_2$ topoisomer by the sequential addition and incubation with fuel strands complementary to the PX set strands to strip the PX set strands from the PX topoisomer followed by addition and incubation with $JX_2$ set strands. To cycle back to the first PX topoisomeric state, the $JX_2$ topoisomer is converted by the sequential addition and incubation with fuel strands complementary to the $JX_2$ set strands to strip $JX_2$ set strands from the $JX_2$ topoisomer followed by addition and incubation with PX set strands.

The present invention further provides an array which includes a plurality of different polynucleic acid nanomechanical devices of the present invention that differ in their nucleotide sequence.

BRIEF DESCRIPTION OF THE DRAWINGS

As shown in FIG. 7A, the PX motif, postulated to be involved in genetic recombination (Shen et al., 1999), consists of two helical domains formed by four strands that flank a central dyad axis (indicated by the vertical black arrows). Two stands are drawn in thin and bold thick lines, where the arrowheads indicate the 3' ends of the strands. The Watson-Crick base pairing in which every nucleotide participates is indicated by the horizontal lines within the two double helical domains. Every possible crossover occurs between the two helical domains. The same conventions apply to the $JX_2$ domain, which lacks two crossovers in the middle. The letters A, B, C and D, show that the bottom of the $JX_2$ motif (C and D) are rotated 180° relative to the PX motif. In FIG. 7B, the two systems, PX and $JX_2$, are also indicated but as closed molecules. Bold thin strand 1 and thin strand 2 are the same for both molecules, but the bold thick set strands, 3 and 4, differ from the light gray thick set strands, 5 and 6. Arrowheads indicate the 3' ends of strands. The complements to strands 3, 4, 5 and 6, containing 5' biotin groups, are the fuel strands for the removal of the set strands. The nucleotide sequences of the strands used for the molecules in Example 2 are presented in Table 1. In FIG. 7C, on the left is a PX molecule. The bold thick set strands are removed by the addition of biotinylated bold thick fuel strands (biotin indicated by black circles) in process I. The unstructured intermediate is converted to the $JX_2$ motif by the addition of the light gray thick set strands in process II. The $JX_2$ molecule is converted to the unstructured intermediate by the addition of biotinylated light gray thick fuel strands in process III. The identity of this intermediate and the one above it is indicated by the identity symbol between them. The cycle is completed by the addition of bold thick set strands in process IV, restoring the PX device. Pairing of the bold thick set strands with their complete conventional complements enables their removal, allowing the introduction of the light gray thick strands into the complex, and switching from the PX to the $JX_2$ state. The PX state can be restored by replacing the light gray thick strands with the bold thick strands ones in a similar way.

FIGS. 8A-8C show gel evidence for the operation of the device. In FIG. 8A, the components of the device in operation are shown on a 14% non-denaturing polyacrylamide gel, run at 20° C. and stained with stains-all dye. The lane LM contains linear length markers derived from HaeIII digestion of pBR322. Device strand sequences have been designed using the program SEQUIN (Seeman et al., 1990) synthesized by routine phosphoramidite techniques (Caruthers et al., 1985) and gel purified. Strands are hybridized at 90° C. (5 min), 65° C. (15 min), 45° C. (30 min), 37° C. (20 min) and 20° C. (30 min) Lane 1 contains the device (1 µM) assembled with PX set strands and lane 4 contains the device (1 µM) assembled with $JX_2$ set strands. Gel mobilities differ because the PX device is likely to have a more compact time-averaged structure than the $JX_2$ device (Sun et al., 1999). Lane 2 contains the products of removing the $JX_2$ set strands from the material in lane 4 and replacing them with set strands corresponding to the PX conformation. Likewise, lane 3 contains the products of removing the PX set strands from the material in lane 1 and replacing them with those corresponding to the $JX_2$ conformation. Note the absence of extraneous products in lanes 2 and 3, indicating the robustness of these transformations.

FIGS. 8B and 8C show cycling of the device through 5 steps beginning either with $JX_2$ (FIG. 8B) or PX (FIG. 8C) as the initial conformation in lane 1. Lanes 2 through 6, respectively, show alternating transformations to the other state. Fuel strands were added to the preformed PX or $JX_2$ at 20° C. and kept at 20° C. for 60 min; the mixture was treated with streptavidin beads at 20° C. for 30 min. to remove the set strand/fuel strand duplexes. After removing the set strands of PX or $JX_2$, the set strands of $JX_2$ or PX molecules were added to the solution and kept at 20° C. for 60 min to establish the device conformation. The addition of fuel strands, followed by set strands, was then repeated three times.

In FIG. 9A, a nondenaturing gel run at 37° C. demonstrates the stability of the intermediate at temperatures well above those used in the experiment using a 14% nondenaturing gel. Lane LM contains linear length markers derived from a HaeIII digestion of pBR322. Lane 1 is the initial conformation of PX (1 µM). Lane 2 contains the intermediate after adding the fuel strands and streptavidin bead treatment to remove the set strands. Lane 3 contains the initial conformation of $JX_2$ (1 µM). Lane 4 contains the intermediate after adding the fuel strands and streptavidin bead treatment to remove the other set of set strands. All samples were warmed at 37° C. for 30 min before loading to the gel. The temperature of the gel was kept at 37° C. using a circulating water bath. In FIG. 9B, a Denaturing gradient gel shows the melting of the intermediate in a 6% segmented perpendicular denaturing gradient gel running at 25° C. with 100% denaturant containing 40% formamide, 7M urea. The relationship between temperature and denaturant concentration is: $T=T_c+0.3\times$Denaturant-Percentage (Abrams et al., 1992). Starting from lane 1 to lane 11, the percentage of the denaturant increases from 0% to 100%, with 10% increases of denaturant in each lane. Each lane contains the intermediate of the device, the intermediate start to dissociate at lane 7, which corresponds to 43° C. Note the intermediate is stable in lane 5, corresponding to 37° C., well above the 20° C. temperature of the experiment in FIGS. 8A-8C.

FIGS. 12A and 12B show PX linear arrays in a cis arrangement, and FIGS. 12C and 12D show $JX_2$ linear arrays in a trans arrangement. FIGS. 12E-12H show three steps of the operation of the device, sampling aliquots from each cycle. The system originates in the PX state (FIG. 12E), and is then converted (left to right) to the $JX_2$ state (FIG. 12F), back to PX (FIG. 12G), and then back to $JX_2$ (FIG. 12H). The PX linear arrays are clearly in the cis arrangement, and the $JX_2$ linear arrays are clearly in the trans arrangement.

FIG. 13A shows the oligonucleotide sequence used to demonstrate the stability of the non-covalent linkages between half-hexagon+device units. The sequence shown (SEQ ID NO:15) contains the same sticky ends and the same flanking sequence as the molecules used in the experiments shown in FIGS. 12A-12H. A non-denaturing gel run at 45° C. showing the stability of the sticky-ended association is shown in FIG. 13B. This is a 10% gel run to test the stability of the 8 base sticky-ended association used in the half-hexagon array. DNA concentration is 1 µM in all lanes. Lane 1 contains strand 1. Lane 2 contains strand 2. Lane 3 contains an annealed sample of strands 1+2. Lane 6 contains strand 3. Lane 7 contains strand 4. Lane 5 contains an annealed sample of strands 3+4. Lane 4 contains an annealed sample of strands 1+2+3+4. Strands are hybridized at 90° C. (5 min), 65° C. (15 min), 45° C. (30 min), Temperature of the gel was controlled to be at 45° C. using a circulating water bath. A denaturing gradient gel showing the melting of the sticky-ends is presented in FIG. 13C. This is a 6% segmented perpendicular denaturing gradient gel run at 37° C. 100% denaturant contains 40% formamide, 7M urea. Starting from lane 1 to lane 9, the percentage of the denaturant increases from 10% to 90%, with 10% increase of denaturant in each lane. Each lane contains the DNA duplex hybridized through the 8 base sticky-ended association. The duplex starts to dissociate in lane 5, which corresponds to 52° C. The sample in lane 4, corresponding to 49° C. is still intact. The relationship between temperature and denaturant concentration is given in the description of FIG. 9B.

DETAILED DESCRIPTION OF THE INVENTION

Watson-Crick (Watson et al., 1953) base pairing is the well-known interaction that stabilizes the coaxial double helical structure of DNA. The complementary relationships between adenine (A) and thymine (T), and between guanine (G) and cytosine (C) provide the means by which the two strands of DNA recognize each other. In addition to double stranded molecules, triple stranded coaxial species can be formed if one of the molecules contains a polypurine tract (Felsenfeld et al., 1957) and the system is properly configured (Frank-Kamenetskii et al., 1995 and Ono et al., 1997). Tetra-stranded coaxial species can be formed that include homopolymer motifs, such as $G_4$ arrangements (e.g., Williamson et al., 1994), the unusual cytosine motif in I-DNA (Gehring et al., 1993), or poly-dA and poly-dT (Chernyi et al., 1990). In addition, multistranded species can be formed that are based on the Holliday junction (Holliday et al., 1964); these molecules contain a unique branch point flanked by three or more double helices (Wang et al., 1991), but the strands are not coaxial in these molecules. McGavin (McGavin, 1971) and Wilson (Wilson, 1979) have proposed paranemic motifs involving a central dyad axis and recognition via hydrogen bonding in the grooves of the helices. Such species are appealing models of homologous recognition, useful to explain recombination data (e.g., Conley et al., 1989), but their formation has not been demonstrated convincingly in the laboratory.

Here, the laboratory of the present inventors report in Example 1 the construction and preliminary physical characterization of a coaxial 4-stranded DNA motif in which every nucleotide is paired by Watson-Crick interactions. In contrast to previously proposed four-stranded parallel molecules, no non-Watson-Crick hydrogen bonding interactions are necessary to stabilize this structure. Similar to the McGavin and Wilson structures, the molecule contains a central dyad axis, relating the backbones of one pair of strands to the other; it also contains two subsidiary DNA helix axes, whose repeat is similar to the normal twist in DNA double helices. The present inventors named this structure paranemic crossover (PX) DNA. The nature of the PX structure is that two double helices associate with each other by exchanging strands of the same polarity at every possible site (Seeman, 2001). Thus, wherever two strands approach the central region of the molecule, they pass over to the other helix, and there are no backbone juxtapositions. Consequently, each strand is involved in a crossover at the start and the end of each of its Watson-Crick helical turns. The period is about twice that of conventional DNA.

Figures 1A, 1B, 1C, 1D:
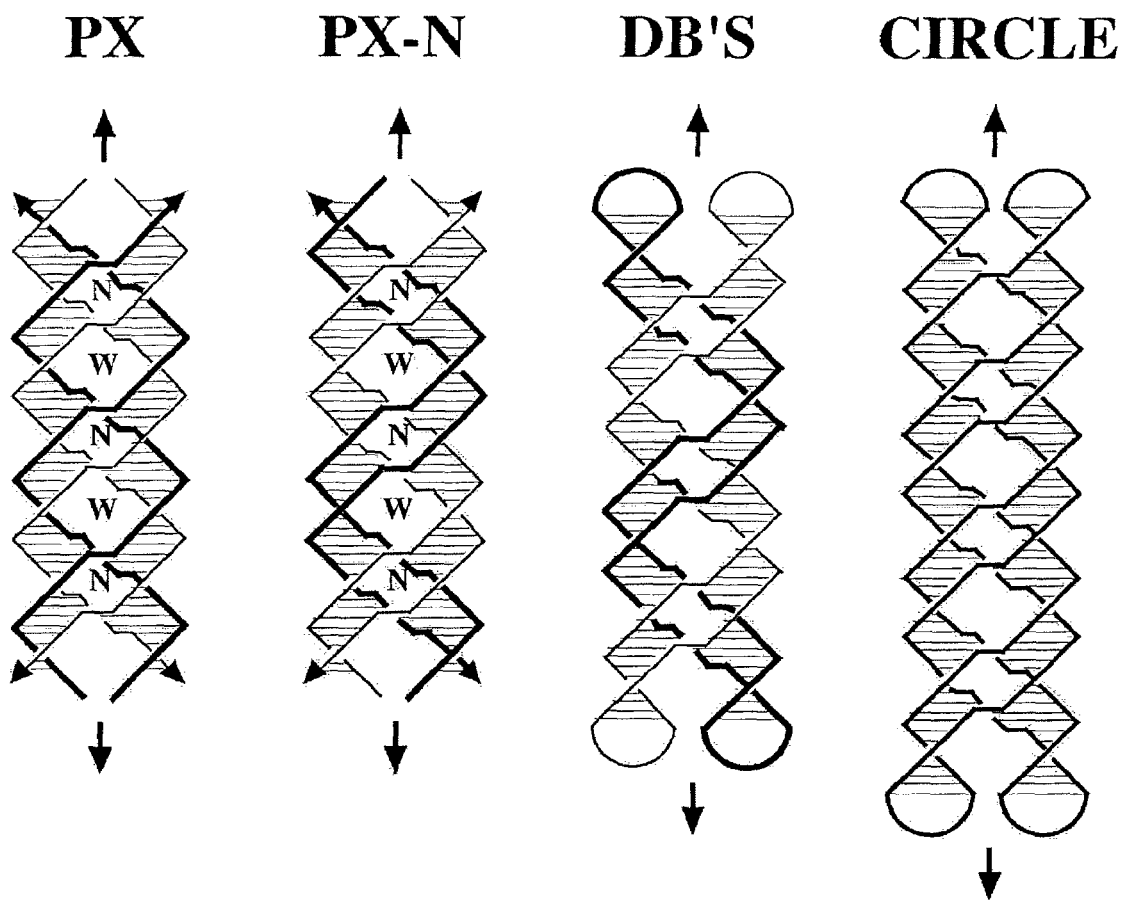
FIGS. 1A-1D show schematic drawings of paranemic crossover DNA, and its closed analogs. The three molecules in FIGS. 1A-1C are drawn containing pairs of strands drawn in thin and bold thick lines; strands drawn with the same thickness are related to each other by the dyad axis. The helix of each strand is approximated by a zig-zag structure. Arrowheads on the strands denote their 3' ends. The base pairs are indicated by very thin horizontal lines. Both the PX (FIG. 1A) and PX-N (FIG. 1B) molecules contain four strands, arranged in two double helical domains related by a central dyad axis. The PX and PX-N molecules are identical, but two different pairs of dyad symmetries are shown between strands flanking the dyad: PX illustrates symmetry between strands of the same polarity, whereas PX-N shows symmetry between strands flanking a minor groove (a third symmetry, between strands flanking the major groove, is not shown). The view is perpendicular to the plane containing both helix axes. The dyad axes are indicated by the short arrows above and below each molecule. The PX and PX-N molecules have alternating major (wide) and minor (narrow) groove tangles, indicated by 'W' and 'N', respectively. The two molecules in FIGS. 1C and 1D are closed PX molecules. The molecule in FIG. 1C contains two paired dumbbells (DB's) that are unlinked topologically. The molecule in FIG. 1D is a half-turn longer in each helical domain and the resulting structure is an intricately self-paired single-stranded circle.

PX DNA, drawn in FIG. 1A, is a generalization of the Holliday intermediate, because it extends the crossover feature over a large range of nucleotide pairs, rather than just a single site. The molecule labeled PX in FIG. 1A shows dyad symmetry between strands of the same polarity; the one labeled PX-N (FIG. 1B) is identical to it, but its symmetry is drawn to suggest two double helices wrapped around each other. How this structure could be involved in cellular processes that involve homology recognition is discussed below.

If one examines the part of the PX molecule flanking the central dyad axis, crossovers occur with alternating frequencies, depending on whether a major groove or a minor groove flanks the axis. In this projection (normal to the plane containing both helix axes), the strands cross each other within the double helices between the inter-helical crossover points; these intra-helix strand crossings, visible as 'X's in FIGS. 1A-1D, are unit tangles (Sumners, 1990) of DNA. These partial turns within each helix are referred to as either a major groove tangle or a minor groove tangle, depending on which of its grooves flanks the central dyad axis. The major (wide) groove tangles are labeled 'W' in FIGS. 1A and 1B, and the minor (narrow) groove tangles are labeled 'N'. The ubiquity of the inter-helix crossovers makes it reasonable to phase the rotational component of each strand's helix from crossover point to crossover point; in going 5' to 3' between crossover points, a strand participates in two unit tangles, first a major groove tangle, and then a minor groove tangle. If the ends of the PX-N (or PX) molecule in FIGS. 1A and 1B were closed, two unlinked dumbbells would be produced, as seen in the molecule labeled DB's (FIG. 1C). However, closing the ends of molecules one unit tangle longer in each helical domain would result in the formation of an intricate, but ultimately trivial knot (a circle), illustrated in FIG. 1D.

Sequence symmetry minimization (Seeman, 1982) was used to model PX molecules in an oligonucleotide system. The laboratory of the present inventors has determined empirically that the best spacing for the minor groove is five nucleotide pairs, but the major groove can contain six, seven or eight nucleotide pairs. The bulk of the experiments in Example 1 apply to three molecules with these features, containing seven half-turns of DNA. The PX motif has been characterized by gel electrophoresis, circular dichroism spectroscopy, thermal transition profiles and hydroxyl radical autofootprinting analysis.

To summarize, paranemic crossover (PX) DNA is a four-stranded coaxial DNA structure containing a central dyad axis that relates two flanking parallel double helices. The strands are held together exclusively by Watson-Crick base pairing. The key feature of the molecule is that the two adjacent parallel DNA double helices form crossovers at every point possible. Hence, reciprocal crossover points flank the central dyad axis at every major or minor groove separation. This motif has been modeled and characterized in an oligonucleotide system; a minor groove separation of 5 nucleotide pairs and major groove separations of 6, 7, or 8 nucleotide pairs produce stable PX DNA molecules. Every strand undergoes a crossover every helical repeat (11, 12 or 13 nucleotides), but the period of each strand corresponds to two helical repeats (22, 24 or 26 nucleotides).

The robust polynucleic acid nanomechanical device of the present invention is based on the nucleic acid paranemic crossover (PX) molecule discussed above and characterized in Example 1, cycling between the PX molecule and its $JX_2$ topoisomer. As it is impossible to switch directly from the PX molecules shown in FIGS. 1A and 1B to the $JX_2$ topoisomer or vice versa because of severe topological problems, the laboratory of the present inventors has created a variant of the PX molecules of FIGS. 1A and 1B, in which one strand in each of the two strand pairs has been broken down into three segments so that the variant PX molecule can be converted directly to its $JX_2$ topoisomer and cycled back again by the sequential addition of different sets of fuel and set strands. Thus, sections of the PX molecule can be removed and replaced with segments lacking two crossovers to form the $JX_2$ topoisomer molecules.

Figure 7A:
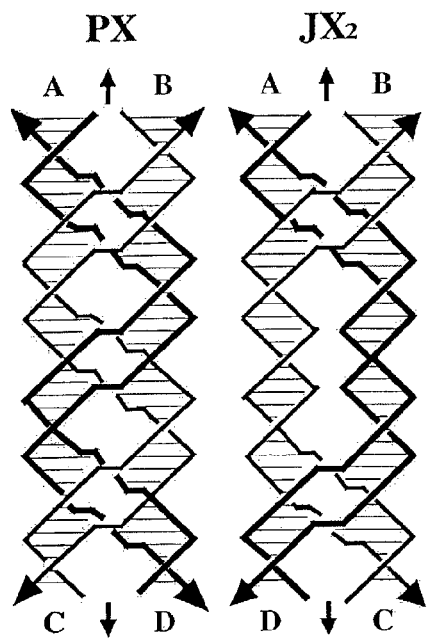
FIGS. 7A-7C show a schematic illustration of the PX and $JX_2$ motifs (FIGS. 7A and 7B) and the principles of device operation (FIG. 7B).
Figure 7B:
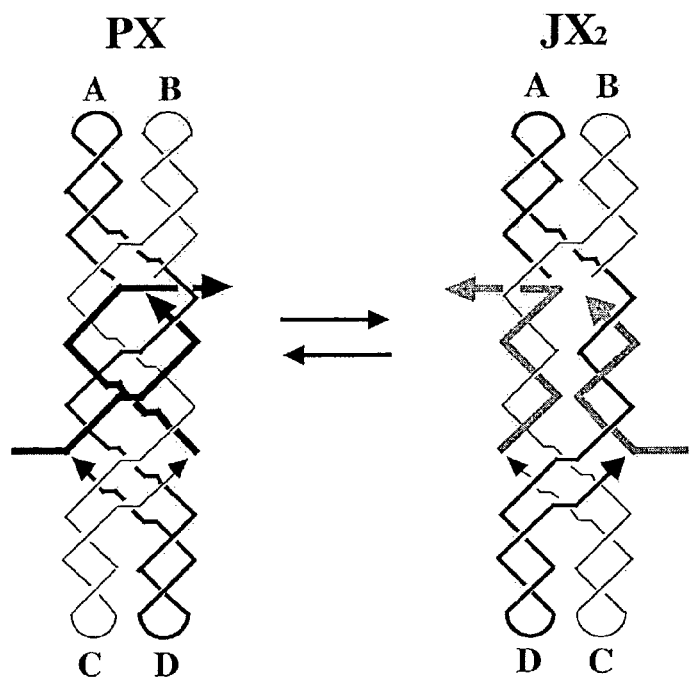

As shown in FIGS. 7A and 7B, the $JX_2$ topoisomer differs from the PX topoisomer in that one pair of ends are rotated 180° relative to the other pair of ends and the $JX_2$ topoisomer has two adjacent sites where two backbones juxtapose without crossing over.

The nanomechanical device of the present invention capable of cycling between two topoisomeric states is formed when a segment, i.e., a middle (internal) segment, of one strand from each strand pair, referred to as a PX set strand ("sets" the state of the device to be in the PX conformation), is broken from the rest of the strand. The nucleic acid paranemic crossover molecule with PX set strands is converted to its $JX_2$ topoisomer by the addition and incubation with fuel stands complementary to the PX set strands to strip the PX set strands from the PX topoisomer (Process I shown in FIG. 7C), producing an unstructured intermediate, followed by addition and incubation with $JX_2$ set strands (Process II in FIG. 7C) to convert the intermediate to the $JX_2$ topoisomer. If the set strands added are not $JX_2$ set strands but rather PX set strands, then the unstructured intermediate can be returned to the PX topoisomeric state instead of being converted to the $JX_2$ topoisomeric state. To cycle back to the PX topoisomeric state, the $JX_2$ topoisomer is converted by addition and incubation with fuel strands complementary to the $JX_2$ set strands to strip the $JX_2$ set strands from the $JX_2$ topoisomer (Process III in FIG. 7C), producing an unstructured intermediate, followed by addition and incubation with PX set strands (Process IV in FIG. 7C) to convert the intermediate to the PX topoisomer. This four process/step cycle thus leads to two robust end points, the PX state and the $JX_2$ state, where the robust nature of the nanomechanical device of the present invention is demonstrated by the absence of any detectable by-products such as dimers. The operation of this device is exemplified in Example 2 and demonstrated by the use of atomic force microscopy.

Preferably, the PX and $JX_2$ set strands have single stranded unpaired extensions at one end thereof so that such extensions can initiate branch migration that leads to removal of the strand from the branched motif. This is because the set strands are paired with their complementary fuel strands along their entire length. Thus, a complement to the entire length of the set stand (termed a "fuel" strand) will pair with it in preference to the partially paired set strand in the PX or $JX_2$ states.

Furthermore, it is preferred that one end of the fuel strands be labeled with a non-nucleic molecule that is a member of a binding pair. This will facilitate the use of the other member of the binding pair, i.e., attached to a solid support, for removal of the fuel strands, either alone or paired with their complementary set strands. Non-limiting examples of binding pairs are ligands and their receptors, antigenic epitopes and antibodies, etc. A preferred embodiment is the labeling of fuel strands at one end thereof with biotin and the use of streptavidin or an avidin-type molecule as the other member of the binding pair for binding biotin.

The ends of the PX molecule and the $JX_2$ topoisomer can be open or closed. When closed, the strand pairs of each helix end are joined together at the ends of the helices to form the closed ends. A restriction enzyme cleavage site can be designed into one or more helical ends. If there is more than one helical end with a restriction enzyme cleavage site, then the restriction enzyme cleavage site can be the same or different at the helical ends. Although these restriction sites can facilitate the joining of the polynucleic acid nanomechanical device of the present invention to an array, such as an array containing other polynucleic acid molecules and/or polynucleic acid nanomechanical devices, restriction sites are not necessary for such joining or insertion to take place. As the polynucleic acid nanomechanical device is sequence dependent, i.e., dependent on the sequence of PX and $JX_2$ set strands, the array in which a device of the present can be inserted can contain a plurality of such polynucleic acid nanomechanical devices with different sequences. An array containing a plurality of different polynucleic acid nanomechanical devices that differ in their nucleotide sequence, preferably in the nucleotide sequences of the PX and $JX_2$ set stands, is intended to be an aspect of the present invention.

It should be appreciated that the terms "nucleic acid" or "polynucleic acid" refer to both DNA and RNA and hybrids of the two. The structure need not resemble anything which can theoretically be made from nature.

A particular oligonucleotide or polynucleotide strand may employ bases other than the standard five, adenine, cytosine, guanine, thymine and uracil. Derivatized (e.g., methylated) and other unusual bases such as iso-guanine, iso-cytosine, amino-adenine, K, X, n, (Piccirilli et al. 1990), inosine and other derivatives of purine and pyrimidine may be used. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction, or where one desires fewer forces holding the strands together.

While the molecules employed in this invention generally have a double stranded region recognized by a restriction endonuclease, the molecules may have virtually anything attached to them. Note that biotinylated DNA has previously been used to assist in attaching a label to DNA used as a hybridization probe. The molecule employed may be quite large and only have a small "tail" of double stranded polynucleotide containing a restriction enzyme cleavage site.

Linkers with plural ends ligatable to plural restriction sites may be employed to link diverse structures. Internal cyclizations are also likely to use a linker. While sticky (staggered) ends on both the structure and the linker are desirable, they are not required. Typically, linkers have at least one portion being a double stranded polynucleotide, but other different chemical moieties are acceptable.

A particular strand need not have a single contiguous ribose-phosphate or deoxyribose-phosphate backbone. One may employ a simple inorganic or organic moiety or polymeric spacer between segments of polynucleotide. Spacers such as polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etc., may be employed. An example of such a hybrid structure is dodecadiol having phophoramidite at one end. This structure has been inserted covalently instead of four T nucleotides to form a hairpin loop in a fashion similar to the nucleotides it replaces. See Mitchel J. Doktycz, Ph.D. Thesis (1991), University of Illinois, Chicago. The term "oligonucleotide", "polynucleotide" and "nucleic acid" are intended to cover all of these structures.

In nature and the field of molecular biology, double stranded DNA generally occurs in the B form. However, for the purposes of this invention it may be desirable for DNA or other double stranded polynucleotide to exist in the A, C, D or Z form. Various bases, derivations and modifications may be used to stabilize the structure in the A, C, D or Z form as well.

Having now generally described the invention, the same will be more readily understood through reference to the following examples which are provided by way of illustration and is not intended to be limiting of the present invention.

EXAMPLE 1

Non-denaturing gel electrophoresis shows that the nucleic acid paranemic crossover (PX) molecules of the present invention are stable, forming well-behaved complexes. PX DNA can be produced from closed dumbbells, demonstrating that the molecule is paranemic. Ferguson analysis indicates that the molecules are similar in shape to DNA double crossover molecules. Circular dichroism spectra are consistent with B-form DNA. Thermal transition profiles suggest a premelting transition in each of the molecules. Hydroxyl radical autofootprinting analysis confirms that there is a crossover point at each of the positions expected in the secondary structure. These molecules are generalized Holliday junctions that have applications in nanotechnology. Experiments relating to PX DNA are described below.

Materials and Methods

Sequence Design: The sequences have been designed by applying the principles of sequence symmetry minimization (Seeman, 1982 and 1990), insofar as it is possible to do so within the constraints of this system. The crossover points on each strand are pre-determined in a PX molecule with an asymmetric sequence: Crossover isomerization (Zhang et al., 1994) would produce mispairing, because major groove tangles would become minor groove tangles and vice versa.

Synthesis and Purification of DNA: All DNA molecules in this study have been synthesized on an Applied Biosystems 380B automatic DNA synthesizer, removed from the support, and deprotected, using routine phosphoramidite procedures (Caruthers, 1985). DNA strands have been purified from denaturing gels.

Formation of Hydrogen-bonded Complexes: Complexes are formed by mixing a stoichiometric quantity of each strand, as estimated by $OD_{260}$, in a solution containing 40 mM Tris.HCl, pH 8.0, 20 mM acetic acid, 2 mM EDTA and 12.5 mM magnesium acetate (TAEMg). This mixture is then heated to 90° C. for 5 minutes and cooled to the desired temperature by the following protocol: 20 minutes at 65° C., 20 minutes at 45° C., 30 minutes at 37° C., 30 minutes at room temperature, and (if desired), 2 hrs at 4° C. Stoichiometry is determined by titrating pairs of strands designed to hydrogen bond together, and visualizing them by native gel electrophoresis; absence of monomer indicates the endpoint.

Thermal Denaturation Profiles. DNA strands are dissolved to 1 mM concentration in 2 ml of a solution containing 40 mM sodium cacodylate and 10 mM magnesium acetate, pH 7.5, and annealed as described above. The samples are transferred to quartz cuvettes, and the cacodylate buffer is used as a blank. Thermal denaturation is monitored at 260 nm on a Spectronic Genesys 5 Spectrophotometer, using a Neslab RTE-111 circulating bath; temperature was incremented at 0.1° C./min.

Hydroxyl Radical Analysis: Individual strands of PX complexes are radioactively labeled, and are additionally gel purified from a 10-20% denaturing polyacrylamide gel. Each of the labeled strands (approximately 1 pmol in 50 mM Tris.HCl (pH 7.5) containing 10 mM $MgCl_2$) is annealed to a tenfold excess of the unlabeled complementary strands, or it is annealed to a tenfold excess of a mixture of the other strands forming the complex, or it is left untreated as a control, or it is treated with sequencing reagents for a sizing ladder. The samples are annealed by heating to 90° C. for 3 min. and then cooled slowly to 4° C. Hydroxyl radical cleavage of the double-strand and PX-complex samples for all strands takes place at 4° C. for 2 min. (Tullius et al., 1985), with modifications noted by Churchill et al. (1988). The reaction is stopped by addition of thiourea. The sample is dried, dissolved in a formamide/dye mixture, and loaded directly onto a 10-20% polyacrylamide/8.3M urea sequencing gel. Autoradiograms are analyzed on a BioRad GS-525 Molecular Imager.

Non-Denaturing Polyacrylamide Gel Electrophoresis: Gels contain 8-20% acrylamide (19:1, crylamide:bisacrylamide). DNA is suspended in 10-25 mL of a solution of TAEMg buffer; the quantities loaded vary as noted. The solution is boiled and allowed to cool slowly in staged decrements to 4° C. Samples are then brought to a final volume of 20 mL and a concentration of 1 mM, with a solution containing TAEMg, 50% glycerol and 0.02% each of Bromophenol Blue and Xylene Cyanol FF tracking dyes. Gels are run on a Hoefer SE-600 gel electrophoresis unit at 11 Volts/cm at 4° C., and stained with Stainsall dye. Absolute mobilities (cm/hr) of native gels run at 4° C. are measured for Ferguson analysis; logarithms are taken to base 10.

Circular Dichroism Spectroscopy: Each of four strands is mixed stoichiometrically to produce a 1 mM solution in a buffer containing in 40 mM Sodium Cacodylate, and 10 mM magnesium acetate at pH 7.5. The strands are annealed as described above. CD spectra are measured using an AVIV (Lakewood, N.J.) model 62A DS spectropolarimeter at room temperature.

Results

Figure 2:
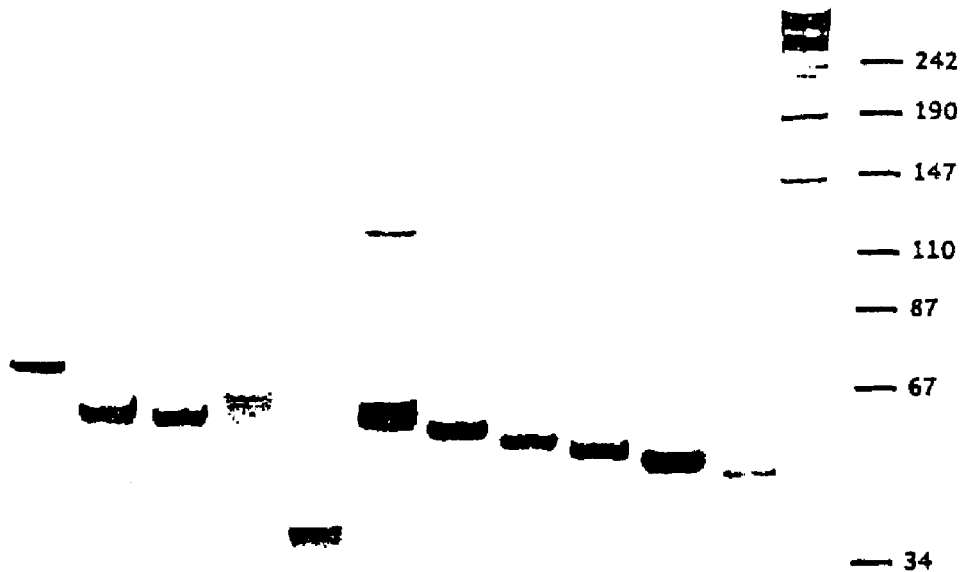
FIG. 2 shows a non-denaturing gel analysis of PX molecules. The 8% non-denaturing gel shown contains variations of the basic PX motif, and illustrates that only 6:5, 7:5 and 8:5 form well behaved molecules. These experiments have been performed with PX molecules and their congeners containing about 5 unit tangles in each helical domain. The contents of each lane is indicated above it. 'E.B.' indicates that the molecule has been treated with ethidium bromide; DB is a dumbbell motif, similar to, but shorter than the two-dumbbell PX molecule in FIG. 1C, in which both molecules have been sealed covalently. In all cases, smears or multimers indicate that PX molecules are not forming stable molecules.

Formation of the Complexes. Complexes are designated as W:N, where W represents the number of nucleotide pairs in the major (wide) groove and N represents the number of nucleotide pairs in the minor (narrow) groove. FIG. 2 illustrates the successful formation of stable 6:5, 7:5 and 8:5 PX complexes containing five half-turns of DNA, and compares them with a series of related molecules of similar length. A single band with approximately the expected mobility is interpreted as a stable molecule. Bands migrating faster than this target are interpreted as breakdown products; well-formed bands migrating more slowly are taken to be multimers of the full complex (containing 8, 12 or more strands), whose presence indicates some form of instability in the 4-strand complex. Lane 1 contains a DAO-type double crossover (DX) molecule (Fu et al., 1993) containing 38 nucleotide pairs per helical domain. Lanes 2 and 3 contain a molecule designed with 6 nucleotide pairs in each groove, 6:6. Neither complex produces a clean single band, but the one in lane 2 contains ethidium, thereby decreasing its twist; the expected molecular band is split, but the molecular dimer prominent in Lane 3 is missing, suggesting that some part of the 6:6 molecule is overtwisted. Lane 4 contains a 7:4 complex, showing a prominent smear below the molecular band, which denotes instability. Lane 5 contains a 6:4 combination, which appears not to form a four-strand complex at all. Lane 6 contains a 9:5 complex, which exhibits multimers. Lanes 7, 8 and 10 contain the stable 8:5, 7:5 and 6:5 complexes, characterized by a single band of roughly the expected molecular weight. Lane 9 contains a PX molecule formed from dumbbells, such as those in FIG. 1C, although shorter; the successful formation of a PX molecule from dumbbell components demonstrates that the topology shown in FIG. 1 is correct, and that plectonemic braiding of individual strands is not required for association. Lane 11 contains another ill-behaved complex, the 5:5 molecule, whose molecular band is split like that in lane 2. The 1:1:1:1 stoichiometry of the complexes has been established by titration (Kallenbach et al., 1983) (data not shown).

Hydroxyl Radical Autofootprinting Analysis. Hydroxyl radical autofootprinting were previously used to characterize unusual DNA molecules, including branched junctions (Wang et al. and Churchill et al., 1988), tethered junctions (Kimball et al., 1990), antijunctions and mesojunctions (Du et al., 2000), and DX molecules (Zhang et al., 1994 and Fu et al., 1993). These experiments are performed by labeling a component strand of the complex and exposing it to hydroxyl radicals. The key feature noted at crossover sites in these analyses is decreased susceptibility to attack when comparing the pattern of the strand as part of the complex, relative to the pattern of the strand derived from linear duplex DNA. Decreased susceptibility is interpreted to suggest that access of the hydroxyl radical may be limited by steric factors at the sites where it is detected. Likewise, similarity to the duplex pattern at points of potential flexure is assumed to indicate that the strand has adopted a conventional helical structure in the complex, whether or not it is required by the secondary structure. In previous studies of junctions, DX molecules, and mesojunctions, protection has been seen particularly at the crossover sites, but also at non-crossover sites where strands from two adjacent parallel or antiparallel domains appear to occlude each other's surfaces, preventing access by hydroxyl radicals (Churchill et al., 1988; Fu et al., 1993; and Du et al., 1992). Thus, crossover sites can be located reliably by hydroxyl radical autofootprinting analysis, but it is not possible to distinguish them unambiguously from juxtapositions of backbone strands.

Figure 3A:
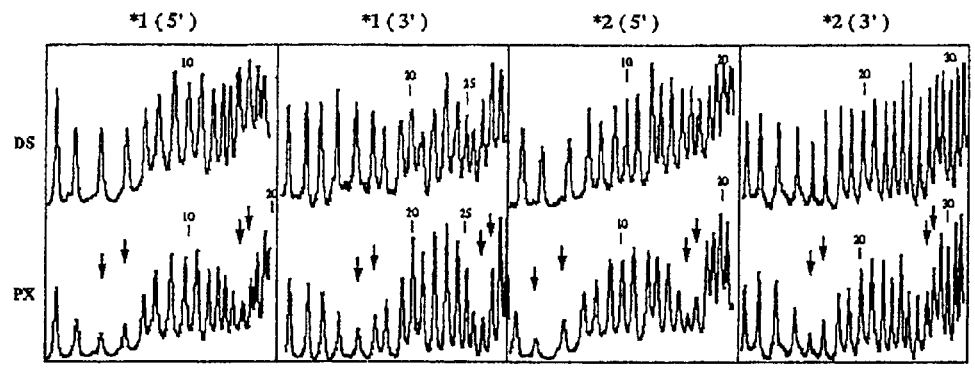
FIGS. 3A-3C show hydroxyl radical autofootprinting of a 6:5 PX molecule. The analysis for each strand is shown twice, once for its 5' end, and once for its 3' end, as indicated above in FIGS. 3A and 3B. Susceptibility to hydroxyl radical attack is compared for each strand when incorporated into the PX molecule (PX) and when paired with its traditional Watson-Crick complement (DS). Nucleotide numbers are indicated above every tenth nucleotide. The two nucleotides flanking expected crossover positions are indicated by two arrows. Note the correlation between the arrows and protection in all cases. The data in FIGS. 3A and 3B are summarized on a molecular drawing in FIG. 3C with strands 1 (SEQ ID NO:1), 2 (SEQ ID NO:2), 3 (SEQ ID NO:3, and 4 (SEQ ID NO:4). Sites of protection are indicated by triangles pointing towards the protected nucleotide; the extent of protection is indicated qualitatively by the sizes of the triangles.
Figure 3B:
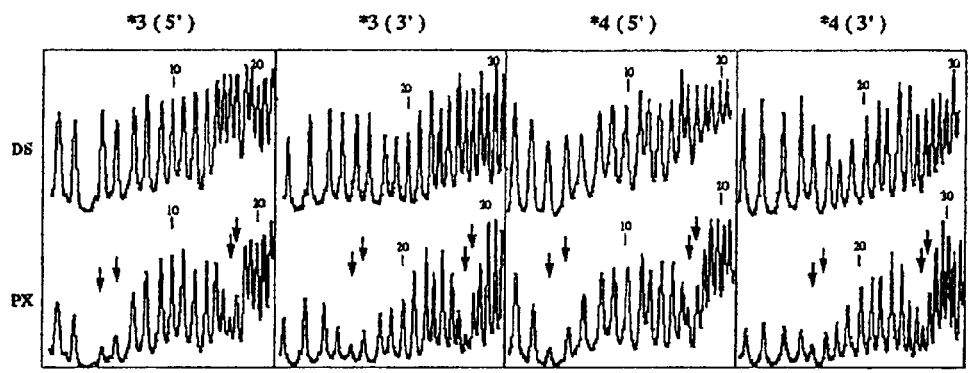
Figure 3C:
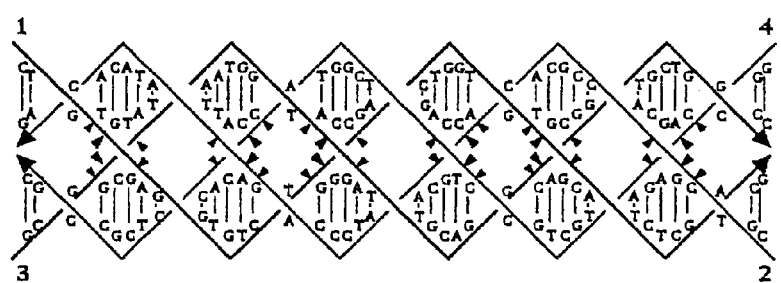

Hydroxyl radical attack patterns are displayed for a 6:5 molecule in FIGS. 3A-3C; results for 7:5 and 8:5 molecules are similar (not shown). The 5' and 3' portions of each strand are shown in two separate panels in FIGS. 3A and 3B, and the expected crossover positions are indicated for each strand by two vertical arrows that indicate the two nucleotides that flank the site. In each panel, the pattern for each strand in the complex (PX) is compared with the pattern for the same strand when it is paired with its conventional Watson-Crick complement in a double helix (DS). Dramatic protection is seen in the vicinity of the crossover point, relative to the duplex control. The protection seen here differs slightly from that seen for branched junctions, where the two nucleotides flanking the crossover point appear to be equally protected. Here, the protection centers primarily on the 5' nucleotide flanking the crossover. This feature was observed in some instances in the hydroxyl radical autofootprinting of parallel DX molecules (Fu et al., 1993). The hydroxyl radical autofootprinting analysis of the PX molecules is in agreement with the expected pattern, with protection visible on each strand in the vicinity of the nucleotides designed to flank crossover points.

Figure 4:
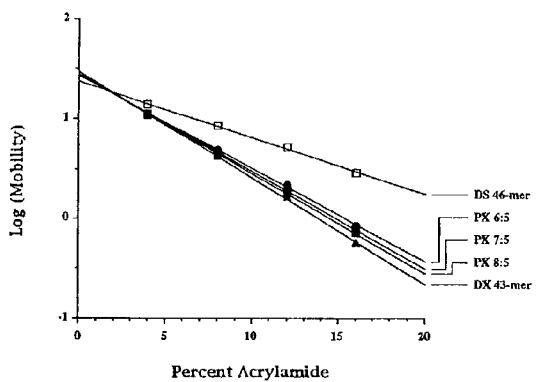
FIG. 4 shows a Ferguson Analysis of PX molecules. The plots of the three PX molecules are compared to a DX molecule of comparable length, which is similar, and to a double helical molecule, which is quite distinct. The slopes and intercepts for the molecules are 6:5 (−0.0934, 1.44), 7:5 (−0.0973, 1.44), 8:5 (−0.0997, 1.45), DX (−0.1065, 1.47), DS (−0.0561, 1.37). Versions of the PX molecules containing juxtapositions flanking their central major groove tangles are similar to the PX molecules: 6:5 (−0.0936, 1.44), 7:5 (−0.0995, 1.45), and 8:5 (−0.1023, 1.46).

Ferguson Analysis. The Ferguson plot is used to analyze log (mobility) as a function of polyacrylamide concentration; the slope of this plot yields information about the friction constant of the molecule. FIG. 4 illustrates Ferguson plots for each of the PX molecules reported here, for a DX control, and for a double stranded control. Each of the PX molecules contains seven unit tangles, so that the 6:5 molecule contains 38 nucleotide pairs per domain, the 7:5 molecule contains 43 nucleotide pairs per domain and the 8:5 molecule contains 46 nucleotide pairs per domain. The slopes of the three PX molecules are very similar to each other, and they are also similar to control molecules in which the central unit tangle is flanked by juxtapositions, rather than crossovers (data not shown). As expected, the slopes increase slightly with the size of the molecule. The slopes are all comparable to that of a DX molecule of similar size, suggesting similarity in their molecular shapes. The duplex molecule plotted along with these species clearly exhibits different frictional properties.

Figure 5:
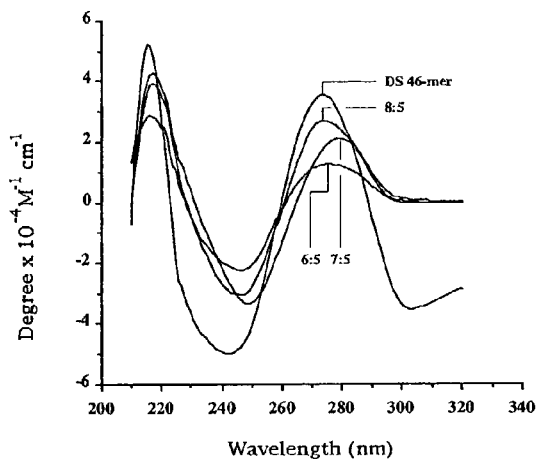
FIG. 5 shows a circular dichroism spectra of PX molecules compared with duplex DNA. The extrema of the double helical 46-mer are similar to those seen for B-DNA. All of the PX spectra are similar to that of the double helical molecule, although the 7:5 molecule is shifted slightly to longer wavelengths.

Circular Dichroism Spectroscopy. The fact that the PX molecule can accommodate three different sizes of the major groove suggests that its secondary structure may be somewhat unusual. This issue was examined qualitatively by measuring circular dichroism spectra for the three PX molecules, and by comparing them to a standard double helical molecule. The spectra (FIG. 5) suggest that none of the molecules have unusual secondary structures, and that they most resemble B-DNA. The long-wavelength maxima are observed at 276 nm (6:5), 279 nm (7:5) and 274 nm (8:5), similar to the duplex standard's maximum at 274 nm. Minima are noted at 246 nm (6:5), 249 nm (7:5) and 247 nm (8:5), again similar to 242 nm, seen for the duplex standard. Thus, the 6:5 and 8:5 PX molecules have extrema most similar to those of B-DNA, whereas the spectra of the 7:5 PX molecules are slightly red-shifted. The key point here, however, is that the stresses placed on the molecules by enforcing the PX structure on them do not appear to have produced a secondary structure significantly different from conventional B-DNA.

Figure 6:
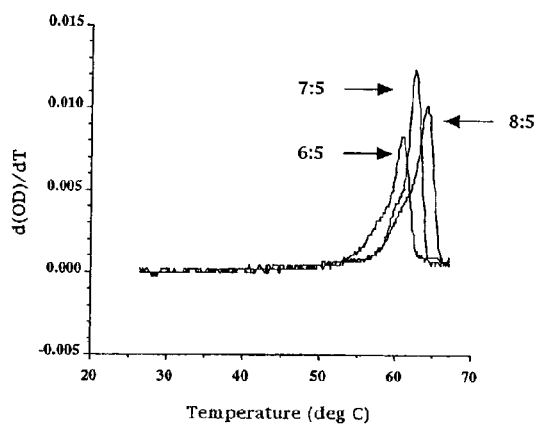
FIG. 6 shows a plot of the thermal transition behavior of PX DNA. The differential melting behavior is shown in a plot smoothed by a 13 point interpolation. It has not been possible to obtain reversible melting curves; hysteresis is always seen, even if the reverse transition is extended to a period of a week. A pre-melting transition is evident for all species.

Thermal transition profiles. FIG. 6 shows the thermal transition profiles of the three complexes as monitored by optical density (260 nm). A differential plot of the melting is shown. The melting temperatures derived from the differential plot are 60.8° C. (6:5), 62.5° C. (7:5) and 64.2° C. (8:5). These relative melting temperatures are in agreement with reasonable expectations, given the relative sizes of the molecules (76, 86 and 92 nucleotide pairs). It is clear that the melting behavior is cooperative, but the differential plot reveals pre-melting transitions for each molecule. It is likely that the melting points represented by the nominal melting temperatures represent the final unstacking of the nucleotides, but that the pre-melting transitions are due to disruption of the PX structure itself.

Discussion

Complex Formation and Stability of Isomers. The data presented suggest that PX DNA is a stable nucleic acid motif containing parallel helix axes that flank a central dyad. Strands with sequences lacking homology that are designed to associate into PX DNA do so as readily as strands designed to form immobile branched junctions (Wang et al., 1991; and Kallenbach et al., 1983) or antiparallel DX molecules (Fu et al., 1993). Indeed, PX DNA with major groove/minor groove ratios of 6:5, 7:5 or 8:5 is better behaved than parallel DX molecules with only two crossovers. Other combinations of major and minor groove sizes do not appear to be stable. The formation of the complexes from a dumbbell analog of 6:5 supports the notion that the complex is paranemic.

Structural Features. The preliminary characterization performed here supports the qualitative structure of the PX molecules drawn in FIG. 1. Hydroxyl radical analysis indicates that each strand exhibits dramatic protection in the vicinity of the expected crossover point, in line with the suggested model. The protection noted is somewhat more intense than that seen previously for juxtapositions in DX molecules (Fu et al., 1993), suggesting that it derives from crossovers. Ferguson analysis confirms that the overall shape of the molecule is similar to that of a DX molecule of comparable size, again in agreement with the model presented in FIG. 1. Circular dichroism spectroscopy indicates that the secondary structure of the DNA is at least qualitatively of the B-form. The spectra are similar to standard B-DNA spectra that have been measured, and differ markedly from, say, A-form spectra, even though the A-structure is traditionally associated with nucleic acids containing 11-12 nucleotide pairs per helical turn.

PX Molecules in DNA Nanotechnology and DNA-Based Computation. The PX molecule is particularly useful in DNA nanotechnology because its structure is amenable to topological variation; one can remove sections of the molecule and replace them with segments lacking two crossovers, shown in FIGS. 7A and 7B as molecules labeled 'JX$_2$'. The bottom helices of the JX$_2$ molecules are rotated 180° relative to the same portion in a pure PX molecule. Recently, the laboratory of the present inventors has used this strategy to produce a robust rotary sequence-dependent nanomechanical device see Example 2 herein; the device is driven by removing the bold thick strands using the method of Yurke et al. (2000), and replacing them with the light gray thick strands. Many different species can be constructed, using different sequences of bold thick strands and light gray thick strands. Thus, this system provides a starting point for DNA-based nanorobotics, because an assembly of N of these devices could, in principle, produce $2^N$ distinct structural states.

The PX motif may have other applications to nanotechnology. The present inventors have suggested that paranemic PX cohesion might be used in place of sticky ends (Seeman, 2001). Antiparallel DNA motifs containing fused helical domains have been suggested as useful elements in DNA-based computation (Winfree, 1996); recently a successful experimental demonstration of this approach has been performed, in which a cumulative XOR calculation was carried out using triple crossover molecules (Mao et al., 1999). It is likely that PX DNA can be applied to this area, possibly with applications to string tiles (Winfree et al., 2001).

EXAMPLE 2

This example demonstrates a robust sequence-dependent rotary DNA device operating in a four-step cycle. It is based on a DNA topological motif, paranemic crossover (PX) DNA (Seeman, 2001; Shen, 1999; and Example 1), and its conversion to a topoisomer (JX2 DNA), in which one end is rotated relative to the other end by 180°.

PX DNA (FIG. 7A) is a 4-stranded motif wherein two parallel double helices are joined by reciprocal exchange (crossing over) of strands at every point where the strands come together (Seeman, 2001 and Shen, 1999). The JX$_2$ motif (FIGS. 7A and 7B) is a topoisomer of PX DNA that contains two adjacent sites where backbones juxtapose without crossing over. The shade and thickness coding of the strands and labels in FIGS. 7A-7C indicates that the top ends, A and B, are the same in both molecules, but the bottom ends, C and D, are rotated 180°. This rotation is the basis for the operation of the device, which uses strand replacement (Yurke et al., 2000) to interconvert the PX and JX$_2$ motifs.

Figure 7C:
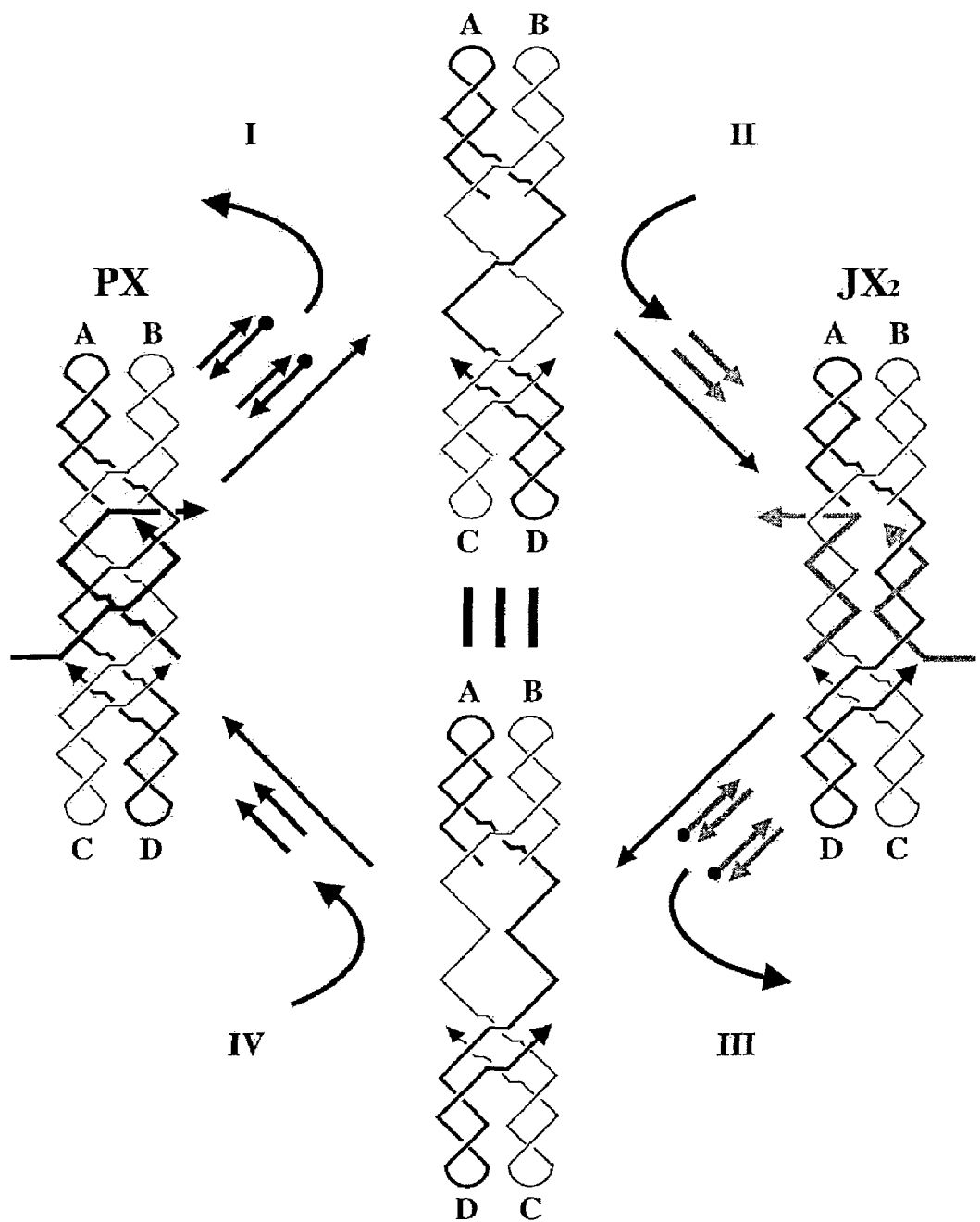

In the device constructed in the laboratory of the present inventors, one strand of each of the thin and bold-thick strand pairs is broken into three strands. The principles of operation are illustrated in FIG. 7C, where the bold thin and thin strands of opposite polarity are shown connected by hairpin loops. Thus, the PX molecule shown there consists of one bold thin strand, one thin strand, and two bold thick strands, termed the 'set' strands, because they set the state of the device to be in the PX conformation; similarly, the JX$_2$ molecule has thick light gray set strands. The set strand associated with the bold thin strand has a 5' single-stranded extension, and the set strand associated with the thin strand has a similar 3' extension. The nucleotide sequence of the strands Yurke et al. (2000) showed that extensions like these can be used to initiate branch migration that leads to removal of the strand from the branched motif, because it is paired with a complementary strand along its entire length. Thus, a complement to the entire length of the set strand (termed a 'fuel' strand) will pair with it in preference to the partially paired set strand in the PX (or JX$_2$) motif.

TABLE 1

Sequences

| | | |
|---|---|---|
| Strand 1: | 5'-TGCCAAGCCTCCAGCCACCTTTTGGTGGCTGGAGGACCGATGCGGCGCGAG TGGTAGGTGCCGAGCACACCTCATGCCTTTTGGCATGAGGTGTATCCGCT-3' | (SEQ ID NO:1) |
| Strand 2: | 5'-CATCGGTTCACCGCACGTCTTTTGACGTGCGGTGACTTGGCAACGGTTGTGA GTACGACAGCGGATCGTCCGAATCACTTTTGTGATTCGGCAGGCTCGGC-3' | (SEQ ID NO:2) |
| Strand 3: | 5'-GCAAGCAGACCTAACTCACACGCCG-3' | (SEQ ID NO:3) |
| Strand 4: | 5'-GTCGTCCACTCGACCGTAGACTAGC-3' | (SEQ ID NO:4) |
| Strand 5: | 5'-GTCGTACTCACAACCGTAGTCTAAC-3' | (SEQ ID NO:5) |
| Strand 6: | 5'-GCTTCCAGACCTACCACTCGCGCCG-3' | (SEQ ID NO:6) |
| Fuel Strand for Strand 3: | 5'-CGGCGTGTGAGTTAGGTCTGCTTGC-3' | (SEQ ID NO:7) |
| Fuel Strand for Strand 4: | 5'-GCTAGTCTACGGTCGAGTGGACGAC-3' | (SEQ ID NO:8) |
| Fuel Strand for Strand 5: | 5'-GTTAGACTACGGTGTGAGTACGAC-3' | (SEQ ID NO:9) |
| Fuel Strand for Strand 6: | 5'-CGGCGCGAGTGGTAGGTCTGGAAGC-3' | (SEQ ID NO:10) |

Process I (FIG. 7C) shows the addition of fuel strand complements to the two bold thick set strands of the PX device, producing the unstructured intermediate at the top of the drawing. Process II shows the addition of light gray thick set strands that convert the intermediate to the $JX_2$ conformation. Process III shows the addition of fuel strands that convert the $JX_2$ molecule to the unstructured intermediate, and process IV shows the addition of the bold thick set strands to produce the PX conformation again. Alternation between a paired structure and a partially unpaired structure analogous to this intermediate characterized the action of the Yurke et al. system. In the device described here, the four-step cycle leads to two robust end points, the PX state and the $JX_2$ state.

Figure 9A:
FIGS. 9A and 9B show the characterization of the thermal properties of the system used in FIGS. 8A-8C.
Figure 9A:
Figure 9B:
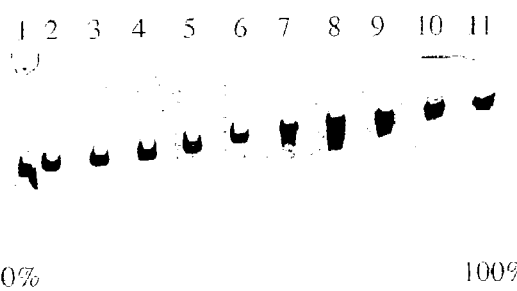

To demonstrate the operation of a robust molecular mechanical device, it is necessary to show both the uniform behavior of the bulk material, and also to visualize the structural transformations of selected molecules. FIG. 8A illustrates the formation and interconversion of both PX and $JX_2$ DNA by non-denaturing gel electrophoresis. All experiments are performed in a buffer containing 40 mM Tris-HCl, pH 8.0, 20 mM acetic acid, 2 mM EDTA and 12.5 mM magnesium acetate (TAEMg); sequences of all molecules used are presented Table 1. The absence of species other than the PX or $JX_2$ molecules (e.g., the dimers noted by Yurke et al., or potential dissociation products) attests to the robustness of the device in bulk. FIGS. 8B and 8C illustrate the cycling of the device between the PX and $JX_2$ states. FIG. 8B shows five steps of operation, beginning in the $JX_2$ state and FIG. 8C shows five steps that begin from the PX state. The intermediate structure is stable at the highest temperatures (20° C.) to which the device has been subjected in this experiment (FIGS. 9A and 9B).

Figure 10:
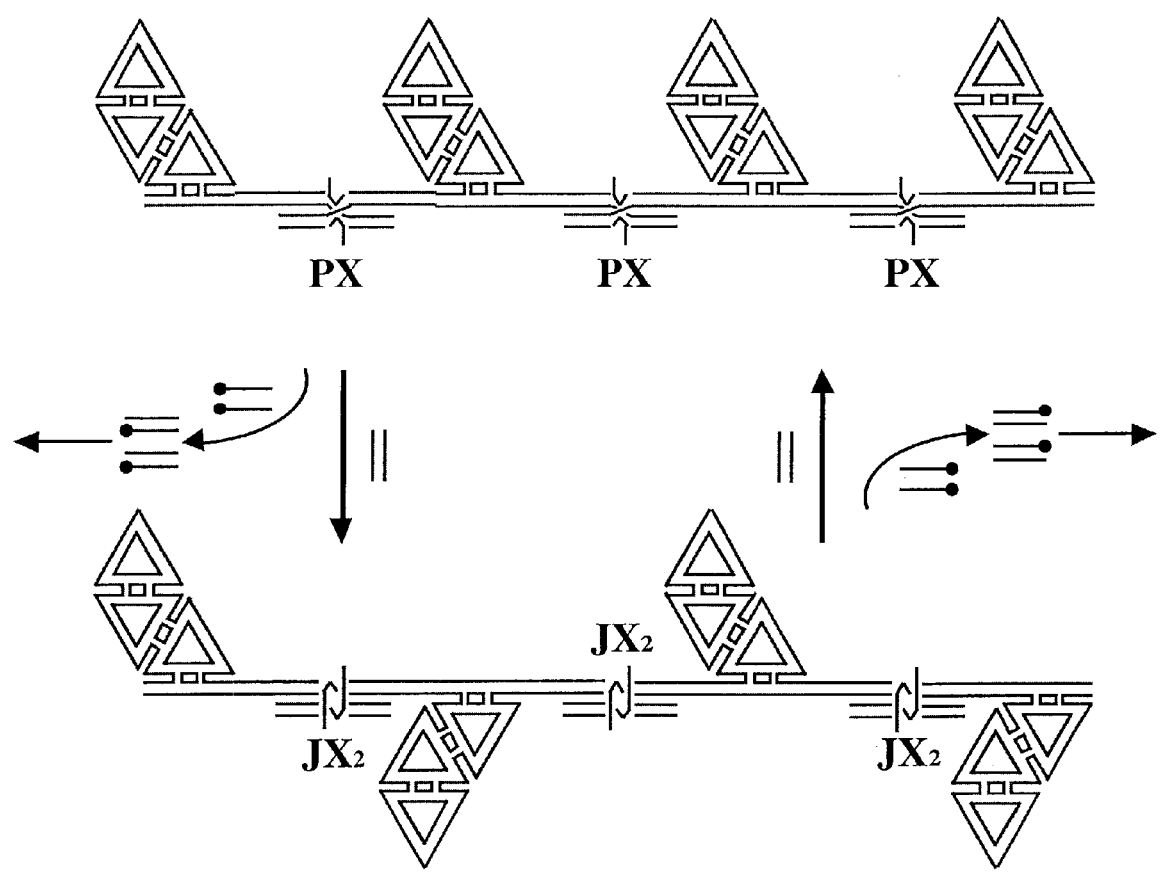
FIG. 10 shows a system to test the device using a highly simplified representation of the system. It consists of a one-dimensional array of half-hexagons joined by the device. Each half-hexagon consists of three edge-sharing DNA triangles (Yang et al., 1998) whose edges are three turns long; the edge-sharing structure is a DNA double crossover molecule, (Fu et al., 1993) which also attaches the half-hexagon to the linear components of the array. The actual strand structure is both more complex and larger than the structure in FIGS. 8A-8C, and is shown in detail in FIGS. 11A and 11B. There are 39 nucleotides between the first device crossover point and the nearest triangle crossover point, a number that was determined empirically to give the most nearly planar structure, although it represents four turns of DNA. In the upper molecule, all of the half-hexagons are aligned pointing in the same direction (cis), whereas they point in opposite directions in the bottom molecule (trans). Biotinylated fuel strands (with black filled circles) are shown removing set strands in both parts of the cycle. Note that relative to the half-hexagon on the left, the third one has rotated 360° and the rightmost one has rotated 540°.
Figure 11A:
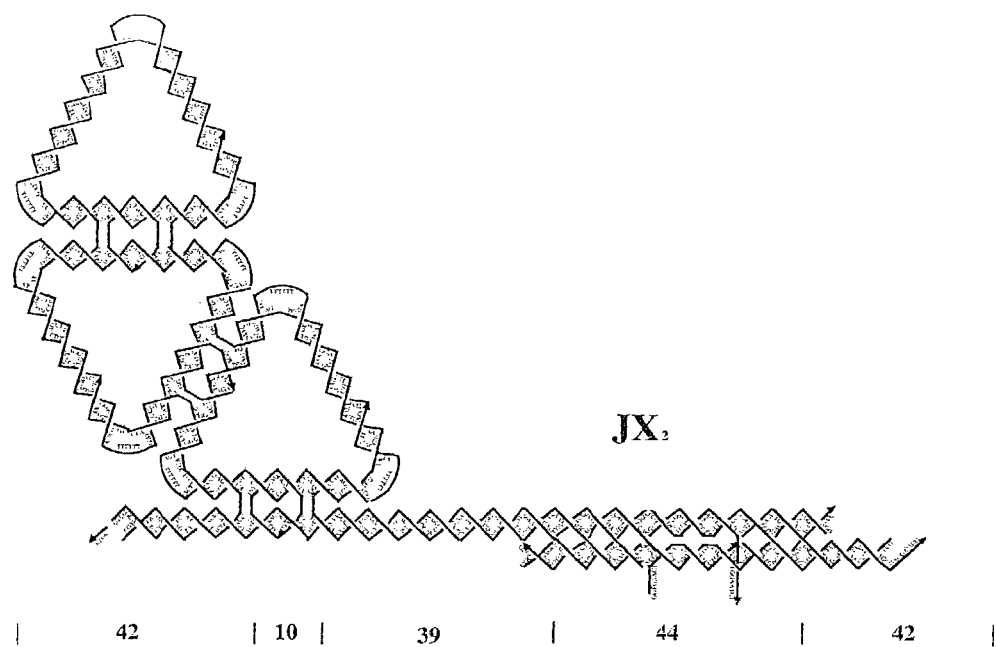
FIGS. 11A and 11B show molecules used in the experiments of FIG. 10. Arrowheads indicate the 3' ends of strands. The PX (FIG. 11B) and the $JX_2$ (FIG. 11A) structures are identical, except for the set strands that control their shapes. The corners of the triangles are $T_6$ sequences, and the cyclic strands involved in the edge-sharing between triangles are covalently closed. The distances between key crossover points are indicated below the structures: 44 nucleotide pairs in each helical domain of the PX structure (four turns containing 5 nucleotides in each minor groove separation and 6 nucleotides in each major groove separation), 39 nucleotide pairs in a four-turn separation (a number established empirically), 10 nucleotide pairs in each domain of a central double crossover structure, and 42 nucleotides in a connecting four-turn separation. Unlike the structures shown in FIGS. 7A-7C, the PX motif used here cannot be constructed from dumbbells. It contains extra crossover points, making it far more stable than the structures illustrated in the other figures.
Figure 11B:
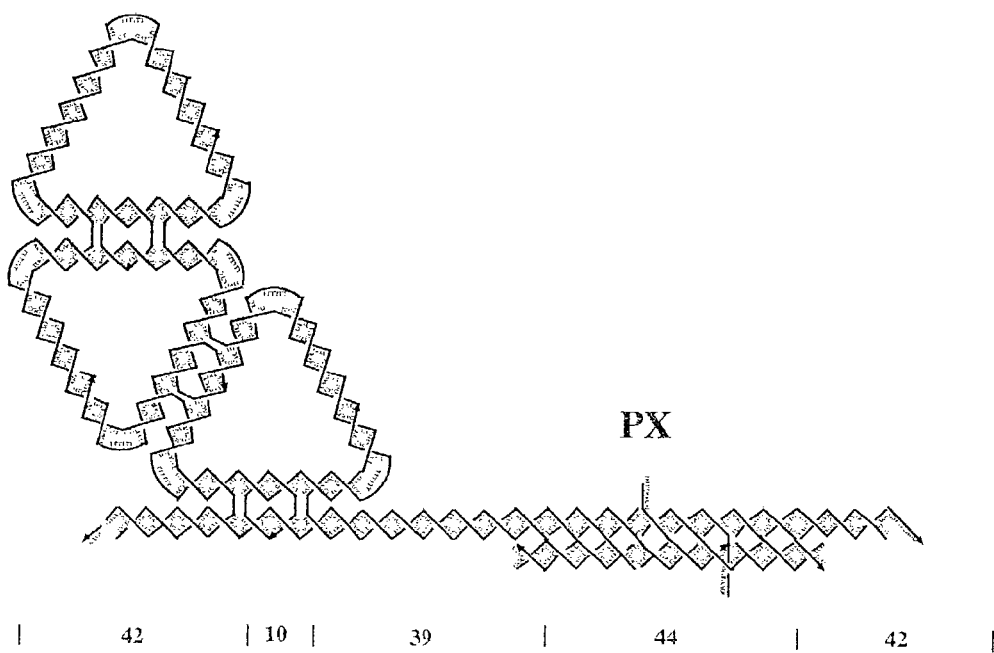

Altered gel mobilities do not guarantee that the construct undergoes the designated structural transformation. This aspect of the device is demonstrated with the system shown in FIG. 10. Half-hexagon markers via edge-sharing between three triangle are constructed; each of the shared edges is a DNA double crossover molecule (Fu et al., 1993). The half-hexagons are connected into one-dimensional oligomeric arrays by linkage through extensions that include PX-$JX_2$ devices. FIG. 10 shows that if the devices are all in the PX state, the half-hexagons have a 'cis' arrangement, where they all point in the same direction. However, when the devices are all in the $JX_2$ state, the half-hexagons form a zig-zag 'trans' structure. FIGS. 11A and 11B show the half-hexagons in PX (FIG. 11B) and $JX_2$ (FIG. 11A) devices in greater detail.

Figure 12A:
FIGS. 12A-12H show Atomic Force Microscopy (AFM) evidence for the operation of the device. All initial species are produced by heating their constituent single strands in boiling water and then cooling in a styrofoam box over a period of 2 days. The 1D arrays of these half-hexagon-plus-device units cohere via 8-nucleotide sticky ends. Non-denaturing gels demonstrate the resistance of this sticky end to disruption at 45° C., where these conversions were performed The images in FIGS. 12A-12D contain control molecules, not devices, that are constrained to be in the PX or $JX_2$ motifs. AFM samples are prepared by placing 1 µL of solution on a piece of freshly cleaved mica (Ted Pella, Inc.), blowing it dry, and washing several times with distilled water. Images are obtained in isopropanol by scanning with a Nanoscope II in contact mode.
Figure 12B:
Figure 12C:
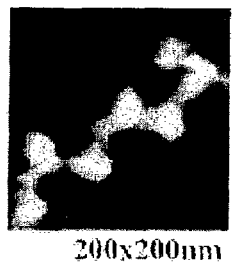
Figure 12D:
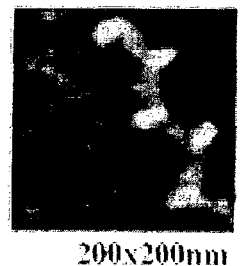
Figure 12E:
Figure 12F:
Figure 12G:
Figure 12H:
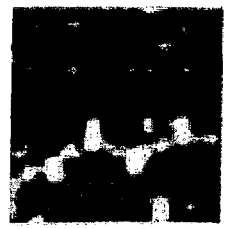
Figure 13A:
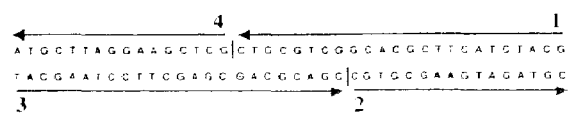
FIGS. 13A-13C show characterization of the thermal properties of the system used in FIGS. 12A-12H.
Figure 13B:
Figure 13C:
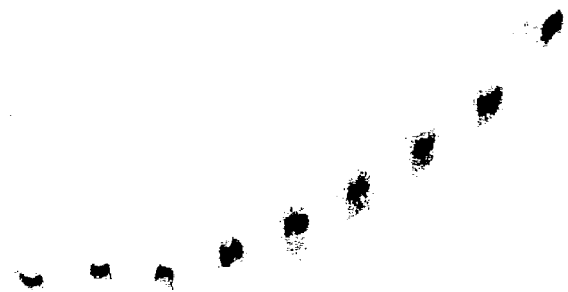

FIGS. 12A-12H visualize the operation of the device by AFM. Two examples are shown for the cis (PX; FIGS. 12A and 12B) and trans (JX2; FIGS. 12C and 12D) systems of FIG. 10, but containing links that are fixed to be PX or $JX_2$ molecules, rather than PX-$JX_2$ devices. The PX state contains a series of half-hexagons extended in a parallel direction, much like the extended fingers of a hand. By contrast, the $JX_2$ state is characterized by a zig-zag arrangement of the half-hexagon extensions. FIGS. 12E-12H illustrate the operation of the device by displaying representative molecules sampled from solutions expected to contain successively (left to right) PX (FIG. 12E), $JX_2$ (FIG. 12F), PX (FIG. 12G) and $JX_2$ (FIG. 12H), states, as the system is cycled. The PX molecules have their half-hexagon markers aligned in a cis arrangement, whereas the markers in the $JX_2$ molecules are all trans. Thus, the system operates as designed, both in bulk and in individual cases. The intermediate state produces a single band on a gel, but it is not well-structured when visualized by AFM (data not shown).

The laboratory of the present inventors have shown that a rotary nanomechanical device is capable of being cycled by the addition of strands that direct its structure. This system is described as being robust, because both end points, the PX state and the $JX_2$ state, are well-defined structures that lack single-stranded regions in structural roles. The extent of motion produced within the rotary device itself will be a function of the distance from its midline, ranging from about 0.4 to 4 nm; however, motions as large as 35 nm have been achieved with the half-hexagon array. Multiple species could be obtained by changing the set strands and the sequences to which they bind. If N different device species of this type can be incorporated into 2D (Winfree et al., 1998 and LaBean et al., 2000) or 3D crystalline arrays, $2^N$ different structural states will be available to the system. Multiple robust states of this sort are necessary for an effective nanorobotics, so that a diversity of shapes can be programmed.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Abrams, E. S. & Stanton, V. P., Jr., Use of denaturing gradient gel electrophoresis to study conformational transitions in nucleic acids, *Meth. Enzymol.* 212, 71-104 (1992)

Brouwer, A. M., Frochot, C., Gatti, F. G., Leigh, D. A., Mottier, L., Paolucci, F., Roffia, S. & Wurpel, G. W. H., Photoinduction of fast, reversible translational motion in a hydrogen-bonded molecular shuttle, *Science* 291, 2124-2128 (2001).

Caruthers, M. H., Gene synthesis machines: DNA chemistry and its uses. Science 230 281-285 (1985).

Chernyi, A. A., Lusov, Y. P., Il'ychova, I. A., Zibrov, A. S., Shchyolkina, A. K., Borisova, O. F., Mamaeva, O. K. & Florntiev, V. L. (1990), *J. Biomol. Str. & Dyns.* 8, 513-527.

Churchill, M. E. A., Tullius, T. D., Kallenbach, N. R. & Seeman, N. C. (1988), *Proc. Nat. Acad. Sci. (USA)* 85, 4653-4656.

Conley, E. C. & West, S. C. (1989), *Cell* 56, 987-995.

Du, S. M., Zhang, S. & Seeman, N. C. (1992), *Biochem.* 31, 10955-10963.

Felsenfeld, G., Davies, D. R. and Rich, A. (1957), *J. Am. Chem. Soc.* 79, 2023-2024.

Frank-Kamenetskii, M. D. & Mirkin, S. M. (1995), *Ann. Rev. Biochem.* 64, 65-96.

Fu, T.-J. & Seeman, N. C., DNA double crossover structures, *Biochem.* 32, 3211-3220 (1993).

Gehring, K., Leroy, J. L. & Gueron M. (1993), A tetrameric DNA structure with protonated cytosine-cytosine base pairs, *Nature* 363, 561-565.

Holliday, R. (1964), *Genet. Res.* 5, 282-304.

Jimenez, M C., Dietrich-Buchecker, C. & Sauvage, J.-P., Towards synthetic molecular muscles: contraction and stretching of a linear-rotaxane dimer, *Angew. Chem. int. Ed.* 39, 3284-3287 (2000).

Kallenbach, N. R., Ma, R.-I. & Seeman, N. C. (1983), *Nature* 305, 829-831.

Kelly, T. R., De Silva, H., Silva, R. A., Unidirectional rotary motion in a molecular system, *Nature* 401, 150-152 (1999).

Kimball, A., Guo, Q., Lu, M., Kallenbach, N. R., Cunningham, R. P., Seeman, N. C. & Tullius, T. D. (1990), *J. Biol. Chem.* 265, 6544-6547.

Koumura, N., Zijlstra, R. W. J., van Delden, R. A., Harada, N., Feringa, B. L., Light-driven monodirectional molecular rotor, *Nature* 401, 152-155 (1999).

LaBean, T. H., Yan, H., Kopatsch, J., Liu, F., Winfree, E., Reif, J. H. & Seeman, N. C., The construction, analysis, ligation and self-assembly of DNA triple crossover complexes, *J. Am. Chem. Soc.* 122, 1848-1860 (2000).

Liu, F., Sha, R. and Seeman, N. C., Modifying the Surface Features of Two-Dimensional DNA Crystals, *J. Am. Chem. Soc.*, 121, 917-922 (1999)

Mao, C., Sun, W., Shen, Z. & Seeman, N. C., A DNA Nanomechanical Device Based on the B-Z Transition, *Nature* 397, 144-146 (1999).

Mao, C., Sun, W., Seeman, N. C., Designed Two-Divisional DNA Holliday Junction Arrays Visualized by Atomic Force Microscopy, *J. Am. Chem. Soc.*, 122, 5437-5443 (1999)

Mao, C., LaBean, T., Reif, J. H., Seeman, N. C., Logical Computation Using Algorithmic Self-Assembly of DNA Tripe Crossover Molecules, *Nature*, 407, 493-496 (2000); *Erratum: Nature*, 408, 750-750 (2000)

McGavin, S. (1971), *J. Mol. Biol.* 55, 293-298.

Ono, A., Ts'O, P. O. P. & Kan, L.-S. (1997), *J. Chin. Chem. Soc.* 44, 601-607.

Pease, A. R., Jeppesen, J. O., Stoddart, J. F., Luo, Y., Collier, C. P. & Heath, J. R., Switching devices based on interlocked molecules, *Accts. Chem. Res.* 34, 433-444 (2001).

Piccirilli et al. 343:33-37, 1990

Seeman, N. C. (1982), *J. Theor. Biol.* 99, 237-247.

Seeman, N. C., De Novo Design of Sequences for Nucleic Acid Structure Engineering, *J. Biomol. Struct. & Dyns.* 8, 573-581 (1990).

Seeman, N. C., DNA Nicks and Nodes and Nanotechnology, *NanoLett.* 1, 22-26 (2001).

Sha, R., Liu, F., Millar, D. P., and Seeman, N. C., Atomic Force Microscopy of Parallel DNA Branched Junction Arrays, *Chem. & Biol.*, 7, 743-751 (2000)

Shen, Z., Ph.D. thesis, New York University, 1999.

Sumners, D. W. (1990), *Math Intelligencer* 12, 71-80.

Sun, W., Mao, C., Iwasaki, H., Kemper, B. & Seeman, N. C., No braiding of Holliday junctions in positively supercoiled DNA molecules, *J. Mol. Biol.* 294, 683-699 (1999).

Tullius, T. D. and Dombroski, B. (1985), *Science* 230, 679-681.

Wang, Y., Mueller, J. E., Kemper, B. & Seeman, N. C. (1991), *Biochem.* 30, 5667-5674.

Watson, J. D. & Crick, F. H. C. (1953), *Nature* 171, 737-738.

Williamson, J. R. (1994), *Ann. Rev. Biophys. & Biomol. Str.* 23, 703-730.

Wilson, J. H. (1979), *Proc. Nat. Acad. Sci. (USA)* 76, 3641-3645.

Winfree E. (1996), In DNA Based Computing, ed. E J Lipton, E B Baum. 199-219. Providence: *Am. Math. Soc.*

Winfree, E., Eng, T. & Rozenberg, G. (2001), In *DNA Computing*, ed. A. Condon, G. Rozenberg, Springer, Berlin, *LNCS.* 2054, 63-88.

Winfree, E., Liu, F., Wenzler, L. A. & Seeman, N. C., Design and self-assembly of two-dimensional DNA crystals, *Nature* 394, 539-544 (1998).

Yang, X., Wenzler, L. A., Qi, J., Li, X. & Seeman, N. C., Ligation of DNA Triangles Containing Double Crossover Molecules, *J. Am. Chem. Soc.* 120, 9779-9786 (1998).

Yurke, B., Turberfield, A. J., Mills, A. P., Jr., Simmel, F. C. & Neumann, J. L, A DNA-fueled molecular machine made of DNA, *Nature* 406, 605-608 (2000).

Zhang, S., and Seeman, N. C., (1994), *J. Mol. Biol.* 238, 658-668.

What is claimed is:

1. A polynucleic acid nanomechanical device capable of cycling between two topoisomeric states upon the sequential addition of fuel and set strands of nucleic acids, comprising a nucleic acid paranemic crossover molecule having a four-stranded coaxial structure of flanking parallel Watson-Crick double helices of nucleic acid strands with two backbones, two pairs of ends, a plurality of major and minor grooves, a central dyad axis, and reciprocal crossovers, where two strands of a strand pair from one helix pass over to the other helix and which reciprocal crossovers flank the central dyad axis at every major and minor groove separation where two strands of a strand pair from one helix approach the central dyad axis, each of said strands being involved in a crossover at the start and end of a Watson-Crick helical turn, wherein:

the device is cycled between said nucleic acid paranemic crossover molecule and its $JX_2$ topoisomer, said $JX_2$ topoisomer differing from said nucleic acid paranemic crossover molecule by having one pair of ends rotated relative to the other pair of ends by 180° and by having two adjacent sites where said two backbones juxtapose without the strands being involved in a crossover; and a segment of a strand from each of said strand pairs of said nucleic acid paranemic crossover molecule, which segment is referred to as a PX set strand and which is broken from the rest of the strand, is stripped from said nucleic acid paranemic crossover molecule by the addition of fuel strands complementary to said PX set strands followed by the addition of $JX_2$ set strands to convert said nucleic acid paranemic crossover molecule to its $JX_2$ topoisomer, said $JX_2$ topoisomer being converted/cycled back to said nucleic acid paranemic crossover molecule by the addition of fuel strands complementary to said $JX_2$ set strands to strip said $JX_2$ set strands from said $JX_2$ topoisomer followed by the addition of PX set strands.

2. The polynucleic acid nanomechanical device of claim 1, wherein the ends of said nucleic acid paranemic crossover molecule are closed.

3. The polynucleic acid nanomechanical device of claim 2, wherein each helix has two ends and the strands of the strand pair are joined together at each of said helix ends to form the closed ends of said nucleic acid paranemic crossover molecule.

4. The polynucleic acid nanomechanical device of claim 1, wherein each helix has two ends and a restriction enzyme cleavage site one or both of said two ends.

5. The polynucleic acid nanomechanical device of claim 4, wherein said restriction enzyme cleavage site is different at each of said two ends.

6. The polynucleic acid nanomechanical device of claim 1, which is joined to an array.

7. The polynucleic acid nanomechanical device of claim 6, wherein said array is an array of polynucleic acid molecules.

8. The polynucleic acid nanomechanical device of claim 7, wherein said array of polynucleic acid molecules is an array having a plurality of polynucleic acid nanomechanical devices with different nucleotide sequences.

9. The polynucleic acid nanomechanical device of claim 1, wherein, in said nucleic acid paranemic crossover molecule, said major groove separation is 6, 7, or 8 nucleotide pairs and said minor groove separation is five nucleotide pairs.

10. The polynucleic acid nanomechanical device of claim 1, wherein every strand undergoes a crossover at every helical repeat of 11, 12, or 13 nucleotides with each strand having a period of two helical repeats that corresponds to 22, 24 or 26 nucleotides.

11. The polynucleic acid nanomechanical device of claim 1, wherein each of said PX set strands and each of said $JX_2$ set strands have a single stranded unpaired extension at one end thereof.

12. The polynucleic acid nanomechanical device of claim 11, wherein the fuel strands complementary to said PX set strands are complementary along the entire length of the PX set strands and the fuel strands complementary to said $JX_2$ set strands are complementary along the entire length of the $JX_2$ set strands.

13. The polynucleic acid nanomechanical device of claim 11, wherein said fuel strands are labeled at one end thereof with a non-nucleic acid molecule that is a member of a binding pair.

14. An array comprising a plurality of different polynucleic acid nanomechanical devices of claim 1, wherein said different polynucleic acid nanomechanical devices differ in nucleotide sequence.

15. The array of claim 14, wherein said different polynucleic acid nanomechanical devices differ in the nucleotide sequences of said PX and $JX_2$ set strands.

* * * * *